United States Patent
Martini et al.

(10) Patent No.: US 9,206,235 B2
(45) Date of Patent: *Dec. 8, 2015

(54) PEPTIDE LINKERS FOR POLYPEPTIDE COMPOSITIONS AND METHODS FOR USING SAME

(71) Applicant: Shire Human Genetic Therapies, Inc., Lexington, MA (US)

(72) Inventors: Paolo Martini, Boston, MA (US); Michael Concino, Bolton, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 24 days.

This patent is subject to a terminal disclaimer.

(21) Appl. No.: 14/078,043

(22) Filed: Nov. 12, 2013

(65) Prior Publication Data

US 2014/0187502 A1    Jul. 3, 2014

Related U.S. Application Data

(63) Continuation of application No. 13/411,287, filed on Mar. 2, 2012, now Pat. No. 8,580,922, and a continuation-in-part of application No. 13/168,969, filed on Jun. 25, 2011, now abandoned, and a continuation-in-part of application No. PCT/US2011/041928, filed on Jun. 25, 2011.

(60) Provisional application No. 61/449,225, filed on Mar. 4, 2011.

(51) Int. Cl.
| | |
|---|---|
| C07K 14/00 | (2006.01) |
| A61K 38/46 | (2006.01) |
| A61K 9/00 | (2006.01) |
| A61K 47/48 | (2006.01) |
| C07K 7/08 | (2006.01) |
| C07K 14/65 | (2006.01) |
| C12N 9/24 | (2006.01) |
| A61K 38/30 | (2006.01) |
| A61K 38/47 | (2006.01) |

(52) U.S. Cl.
CPC ............... *C07K 14/00* (2013.01); *A61K 38/30* (2013.01); *A61K 38/465* (2013.01); *A61K 38/47* (2013.01); *A61K 47/48338* (2013.01); *C07K 7/08* (2013.01); *C07K 14/65* (2013.01); *C12N 9/2402* (2013.01); *C12Y 302/0105* (2013.01); *A61K 9/0019* (2013.01); *C07K 2319/01* (2013.01)

(58) Field of Classification Search
None
See application file for complete search history.

(56) References Cited

U.S. PATENT DOCUMENTS

| | | |
|---|---|---|
| 7,569,376 B2 | 8/2009 | Bayer et al. |
| 8,580,922 B2 | 11/2013 | Martini et al. |
| 2007/0061916 A1 | 3/2007 | Kovalic et al. |
| 2008/0171852 A9 | 7/2008 | Kim et al. |
| 2008/0279765 A1 | 11/2008 | Chettibi et al. |
| 2010/0075906 A1 | 3/2010 | Lebowitz et al. |
| 2010/0233095 A1 | 9/2010 | Duan et al. |
| 2010/0249021 A1 | 9/2010 | Gao et al. |
| 2011/0318327 A1 | 12/2011 | Concino et al. |

FOREIGN PATENT DOCUMENTS

| | | |
|---|---|---|
| WO | WO 2007/141346 | 12/2007 |
| WO | WO 2009/137721 | 11/2009 |
| WO | WO 2011/163652 | 12/2011 |
| WO | WO 2012/122042 | 9/2012 |

OTHER PUBLICATIONS

LeBowitz, et al., "Glycosylation-independent targeting enhances enzyme delivery to lysosomes and decreases storage in mucopolysaccharidosis type VII mice" PNAS, 2004, 101:9; 3083-3088.
Stuart Kornfeld, "Lysosomal enzyme targeting" Biochemical Society Transactions, 1990, 18:367-374.
Araki, et al., HrpW. GenBank Accession No. Q201N6. Oct. 31, 2006. [Retrieved from the internet on Nov. 5, 2012] <url:http://www.ncbi.nlm.nih.gov/protein/g20in6>.
Egerer et al. "Secreted antiviral entry inhibitory (SAVE) peptides for gene therapy of infection", Mol. Ther.; 19,(7): 1236-1244 (2011).
Wriggers et al. "Control of protein functional dynamics by peptide linkers" Biopolymers; 2005; vol. 80, No. 6; pp. 736-746.
Robinson, CR, et al., Optimizing the stability of single-chain proteins by linker length and composition mutagenesis. Proceedings of the National Academy of Sciences, 1998. 5929-5934.
International Search Report for International Application PCT/US2012/027561, dated Nov. 26, 2012.
Non-Final Office Action for U.S. Appl. No. 13/411,287, dated Dec. 27, 2012.
Chichili, V.P.R. et al., Linkers in the structural biology of protein-protein interactions, Protein Science, 22(2): 153-167 (2013).

(Continued)

*Primary Examiner* — David J Steadman
*Assistant Examiner* — Paul Holland
(74) *Attorney, Agent, or Firm* — Choate, Hall & Stewart LLP; Fangli Chen; Rolando Medina

(57) ABSTRACT

Disclosed herein are novel peptide linkers and polypeptide compositions comprising the linkers (e.g., chimeric polypeptides) and methods of using the polypeptide compositions. The compositions and methods are particularly useful for targeting/delivering a polypeptide or protein of interest (e.g., a therapeutic polypeptide) to a cell, tissue or organ of interest in order to treat various diseases or disorders (e.g., lysosomal storage disorders).

22 Claims, 15 Drawing Sheets

(56) References Cited

OTHER PUBLICATIONS

George, R. A. and Heringa, J., An analysis of protein domain linkers: their classification and role in protein folding, Protein Engineering, 15(11): 871-879 (2002).

Sinow, C. S., Construction of an IGF-NAGLU Fusion Protein for Treatment of Sanfilippo B Syndrome, California State Science Fair, 2008 Project Summary, Project No. S0417: 1 page (2008), Retrieved from the Internet [Feb. 12, 2015], URL: https:jjwvvw.usc.edu/CSSF/History/2008/ProjectsjS0417.pdf.

FIG.1

GAPGGGGGAAAAAGGGGG (SEQ ID NO. 1)

FIG. 2

```
GAPGGGGGAAAAAGGGGG
GAPGGGGGAAAAAGGGGG
GAPGGGGGAAAAAGGGGG
GAP  (SEQ ID NO. 2)
``` pXD671-NAGLU pXD671-NAGLU-IGFII

Linker:
...G-A-P...

pXD671-NAGLU-GAG₃-IGFII

Linker:
...G-A-P-G-G-G-G-G-A-A-A-A-A-G-G-G-G-G-
G-A-P-G-G-G-G-G-A-A-A-A-A-G-G-G-G-G-
G-A-P-G-G-G-G-G-A-A-A-A-A-G-G-G-G-G-
G-A-P...
(SEQ ID NO. 2)

FIG. 4A

```
ATGGAGGCGGTGGCGGTGGCCGCGGCGGTGGGGGTCCTTCTCCTGGCCG
GGGCCGGGGGCGCGGCAGGCGACGAGGCCCGGGAGGCGGCGGCCGTGCG
GGCGCTCGTGGCCCGGCTGCTGGGCCAGGCCCCGCGGCCGACTTCTCC
GTGTCGGTGGAGCGCGCTCTGGCTGCCAAGCCGGGCTTGGACACCTACA
GCCTGGGCGGCGGCGGCGCGGCGCGCGTGCGGGTGCGCGGCTCCACGGG
CGTGGCGGCCGCCGCGGGCTGCACCGCTACCTGCGCGACTTCTGTGGC
TGCCACGTGGCCTGGTCCGGCTCTCAGCTGCGCCTGCCGCGGCCACTGC
CAGCCGTGCCGGGGGAGCTGACCGAGGCCACGCCCAACAGGTACCGCTA
TTACCAGAATGTGTGCACGCAAAGCTACTCCTTCGTGTGGTGGGACTGG
GCCCGCTGGGAGCGAGAGATAGACTGGATGGCGCTGAATGGCATCAACC
TGGCACTGGCCTGGAGCGGCCAGGAGGCCATCTGGCAGCGGGTGTACCT
GGCCTTGGGCCTGACCCAGGCAGAGATCAATGAGTTCTTTACTGGTCCT
GCCTTCCTGGCCTGGGGGCGAATGGGCAACCTGCACACCTGGGATGGCC
CCCTGCCCCCCTCCTGGCACATCAAGCAGCTTTACCTGCAGCACCGGGT
CCTGGACCAGATGCGCTCCTTCGGCATGACCCCAGTGCTGCCTGCATTC
GCGGGGCATGTTCCCGAGGCTGTCACCAGGGTGTTCCCTCAGGTCAATG
TCACGAAGATGGGCAGTTGGGGCCACTTTAACTGTTCCTACTCCTGCTC
CTTCCTTCTGGCTCCGGAAGACCCCATATTCCCCATCATCGGGAGCTCT
TCCTGCGAGAGCTGATCAAAGAGTTTGGCACAGACCACATCTATGGGGC
CGACACTTTCAATGAGATGCAGCCACCTTCCTCAGAGCCCTCCTACCTT
GCCGCAGCCACCACTGCCGTCTATGAGGCCATGACTGCAGTGGATACTG
AGGCTGTGTGGCTGCTCCAAGGCTGGCTCTTCCAGCACCAGCCGCAGTT
CTGGGGGCCCGCCCAGATCAGGGCTGTGCTGGGAGCTGTGCCCCGTGGC
CGCCTCCTGGTTCTGGACCTGTTTGCTGAGAGCCAGCCTGTGTATACCC
GCACTGCCTCCTTCCAGGGCCAGCCCTTCATCTGGTGCATGCTGCACAA
CTTTGGGGGAAACCATGGTCTTTTTGGAGCCCTAGAGGCTGTGAACGGA
GGCCCAGAAGCTGCCCGCCTCTTCCCCAACTCCACCATGGTAGGCACGG
GCATGGCCCCGAGGGCATCAGCCAGAACGAAGTGGTCTATTCCCTCAT
GGCTGAGCTGGGCTGGCGAAAGGACCCAGTGCCAGATTTGGCAGCCTGG
GTGACCAGCTTTGCCGCCCGGCGGTATGGGGTCTCCCACCCGGACGCAG
GGGCAGCGTGGAGGCTACTGCTCCGGAGTGTGTACAACTGCTCCGGGGA
GGCCTGCAGGGGCCACAATCGTAGCCCGCTGGTCAGGCGGCCGTCCCTA
CAGATGAATACCAGCATCTGGTACAACCGATCTGATGTGTTTGAGGCCT
GCGGCTGCTGCTCACATCTGCTCCCTCCCTGGCCACCAGCCCCGCCTT
CCGCTACGACCTGCTGGACCTCACTCGGCAGGCAGTGCAGGAGCTGGTC
AGCTTGTACTATGAGGAGGCAAGAAGCGCCTACCTGAGCAAGGAGCTGG
CCTCCCTGTTGAGGGCTGGAGGCGTCCTGGCCTATGAGCTGCTGCCGGC
ACTGGACGAGGTGCTGGCTAGTGACAGCCGCTTCTTGCTGGGCAGCTGG
CTAGAGCAGGCCCGAGCAGCGGCAGTCAGTGAGGCCGAGGCCGATTTCT
ACGAGCAGAACAGCCGCTACCAGCTGACCTTGTGGGGGCCAGAAGGCAA
```

FIG. 4A (CONT.)

CATCCTGGACTATGCCAACAAGCAGCTGGCGGGGTTGGTGGCCAACTAC
TACACCCCTCGCTGGCGGCTTTTCCTGGAGGCGCTGGTTGACAGTGTGG
CCCAGGGCATCCCTTTCCAACAGCACCAGTTTGACAAAAATGTCTTCCA
ACTGGAGCAGGCCTTCGTTCTCAGCAAGCAGAGGTACCCCAGCCAGCCG
CGAGGAGACACTGTGGACCTGGCCAAGAAGATCTTCCTCAAATATTACC
CCCGCTGGGTGGCCGGCTCTTGG (SEQ ID NO. 3)

FIG. 4B

MEAVAVAAAVGVLLLAGAGGAAGDEAREAAAVRALVARLLGPGPAADFS
VSVERALAAKPGLDTYSLGGGGAARVRVRGSTGVAAAAGLHRYLRDFCG
CHVAWSGSQLRLPRPLPAVPGELTEATPNRYRYYQNVCTQSYSFVWWDW
ARWEREIDWMALNGINLALAWSGQEAIWQRVYLALGLTQAEINEFFTGP
AFLAWGRMGNLHTWDGPLPPSWHIKQLYLQHRVLDQMRSFGMTPVLPAF
AGHVPEAVTRVFPQVNTKMGSWGHFNCSYCSFLLAPEDPIFPIIGSL
FLRELIKEFGTDHIYGADTFNEMQPPSSEPSYLAAATTAVYEAMTAVDT
EAVWLLQGWLFQHQPQFWGPAQIRAVLGAVPRGRLLVLDLFAESQPVYT
RTASFQGQPFIWCMLHNFGGNHGLFGALEAVNGGPEAARLFPNSTMVGT
GMAPEGISQNEVVYSLMAELGWRKDPVPDLAAWVTSFAARRYGVSHPDA
GAAWRLLLRSVYNCSGEACRGHNRSPLVRRPSLQMNTSIWYNRSDVFEA
WRLLLTSAPSLATSPAFRYDLLDLTRQAVQELVSLYYEEARSAYLSKEL
ASLLRAGGVLAYELLPALDEVLASDSRFLLGSWLEQARAAAVSEAEADF
YEQNSRYQLTLWGPEGNILDYANKQLAGLVANYYTPRWLFLEALVDSV
AQGIPFQQHQFDKNVFQLEQAFVLSKQRYPSQPRGDTVDLAKKIFLKYY
PRWVAGSW (SEQ ID NO. 4)

FIG. 5A

CTTTGCGGCGGGGAGCTGGTGGACACCCTCCAGTTCGTCTGTGGGGACC
GCGGCTTCTACTTCAGCAGGCCCGCAAGCCGTGTGAGCCGTCGCAGCCG
TGGCATCGTTGAGGAGTGCTGTTTCCGCAGCTGTGACCTGGCCCTCCTG
GAGACGTACTGTGCTACCCCGCCAAGTCCGAGTGA (SEQ ID NO. 5)

FIG. 5B

LCGGELVDTLQFVCGDRGFYFSRPASRVSRRSRGIVEECCFRSCDLALL
ETYCATPAKSE (SEQ ID NO. 6)

FIG. 6

GGGGGAAAAAGGGGG (SEQ ID NO. 7)

FIG. 7

MEAVAVAAAVGVLLLAGAGGAAGDEAREAAAVRALVARLLGPGPAADFS
VSVERALAAKPGLDTYSLGGGGAARVRVRGSTGVAAAAGLHRYLRDFCG
CHVAWSGSQLRLPRPLPAVPGELTEATPNRYRYYQNVCTQSYSFVWWDW
ARWEREIDWMALNGINLALAWSGQEAIWQRVYLALGLTQAEINEFFTGP
AFLAWGRMGNLHTWDGPLPPSWHIKQLYLQHRVLDQMRSFGMTPVLPAF
AGHVPEAVTRVFPQVNVTKMGSWGHFNCSYSCSFLLAPEDPIFPIIGSL
FLRELIKEFGTDHIYGADTFNEMQPPSSEPSYLAAATTAVYEAMTAVDT
EAVWLLQGWLFQHQPQFWGPAQIRAVLGAVPRGRLLVLDLFAESQPVYT
RTASFQGQPFIWCMLHNFGGNHGLFGALEAVNGGPEAARLFPNSTMVGT
GMAPEGISQNEVVYSLMAELGWRKDPVPDLAAWVTSFAARRYGVSHPDA
GAAWRLLLRSVYNCSGEACRGHNRSPLVRRPSLQMNTSIWYNRSDVFEA
WRLLLTSAPSLATSPAFRYDLLDLTRQAVQELVSLYYEEARSAYLSKEL
ASLLRAGGVLAYELLPALDEVLASDSRFLLGSWLEQARAAAVSEAEADF
YEQNSRYQLTLWGPEGNILDYANKQLAGLVANYYTPRWRLFLEALVDSV
AQGIPFQQHQFDKNVFQLEQAFVLSKQRYPSQPRGDTVDLAKKIFLKYY
PRWVAGSWGAPLCGGELVDTLQFVCGDRGFYFSRPASRVSRRSRGIVEE
CCFRSCDLALLETYCATPAKSE (SEQ ID NO. 8)

FIG. 8

MEAVAVAAAVGVLLLAGAGGAAGDEAREAAAVRALVARLLGPGPAADFS
VSVERALAAKPGLDTYSLGGGGAARVRVRGSTGVAAAAGLHRYLRDFCG
CHVAWSGSQLRLPRPLPAVPGELTEATPNRYRYYQNVCTQSYSFVWWDW
ARWEREIDWMALNGINLALAWSGQEAIWQRVYLALGLTQAEINEFFTGP
AFLAWGRMGNLHTWDGPLPPSWHIKQLYLQHRVLDQMRSFGMTPVLPAF
AGHVPEAVTRVFPQVNVTKMGSWGHFNCSYSCSFLLAPEDPIFPIIGSL
FLRELIKEFGTDHIYGADTFNEMQPPSSEPSYLAAATTAVYEAMTAVDT
EAVWLLQGWLFQHQPQFWGPAQIRAVLGAVPRGRLLVLDLFAESQPVYT
RTASFQGQPFIWCMLHNFGGNHGLFGALEAVNGGPEAARLFPNSTMVGT
GMAPEGISQNEVVYSLMAELGWRKDPVPDLAAWVTSFAARRYGVSHPDA
GAAWRLLLRSVYNCSGEACRGHNRSPLVRRPSLQMNTSIWYNRSDVFEA
WRLLLTSAPSLATSPAFRYDLLDLTRQAVQELVSLYYEEARSAYLSKEL
ASLLRAGGVLAYELLPALDEVLASDSRFLLGSWLEQARAAAVSEAEADF
YEQNSRYQLTLWGPEGNILDYANKQLAGLVANYYTPRWRLFLEALVDSV
AQGIPFQQHQFDKNVFQLEQAFVLSKQRYPSQPRGDTVDLAKKIFLKYY
PRWVAGSWGAPGGGGGAAAAGGGGGAPGGGGGAAAAGGGGGAPGG
GGGAAAAGGGGGAPLCGGELVDTLQFVCGDRGFYFSRPASRVSRRSR
GIVEECCFRSCDLALLETYCATPAKSE (SEQ ID NO. 9)

FIG. 12

GGGGGSSSSSGGGGG (SEQ ID NO. 10)

FIG. 13

GAP (SEQ ID NO. 11)

FIG. 14

GGGGGP (SEQ ID NO. 12)

SEQUENCE LISTING

```
<160> NUMBER OF SEQ ID NOS: 12

<210> SEQ ID NO 1
<211> LENGTH: 18
<212> TYPE: PRT
<213> ORGANISM: Artificial
<220> FEATURE:
<223> OTHER INFORMATION: Peptide Linker

<400> SEQUENCE: 1

Gly Ala Pro Gly Gly Gly Gly Ala Ala Ala Ala Ala Gly Gly Gly
1               5                   10                  15

Gly Gly

<210> SEQ ID NO 2
<211> LENGTH: 57
<212> TYPE: PRT
<213> ORGANISM: Artificial
<220> FEATURE:
<223> OTHER INFORMATION: Peptide Linker

<400> SEQUENCE: 2

Gly Ala Pro Gly Gly Gly Gly Ala Ala Ala Ala Ala Gly Gly Gly
1               5                   10                  15

Gly Gly Gly Ala Pro Gly Gly Gly Gly Ala Ala Ala Ala Ala Gly
            20                  25                  30

Gly Gly Gly Gly Ala Pro Gly Gly Gly Gly Ala Ala Ala Ala
        35                  40                  45

Ala Gly Gly Gly Gly Gly Gly Ala Pro
```

<210> SEQ ID NO 3
<211> LENGTH: 2228
<212> TYPE: DNA
<213> ORGANISM: Artificial
<220> FEATURE:
<223> OTHER INFORMATION: NaGlu-IGFII Fusion Construct

<400> SEQUENCE: 3

```
atggaggcgg tggcggtggc cgcggcggtg ggggtccttc tcctggccgg ggccgggggc      60
gcggcaggcg acgaggcccg ggaggcggcg ccgtgcggg cgctcgtggc ccggctgctg     120
gggccaggcc ccgcggccga cttctccgtg tcggtggagc gcgctctggc tgccaagccg     180
ggcttggaca cctacagcct gggcggcggc ggcgcggcgc gcgtgcgggt gcgcggctcc     240
acgggcgtgg cggccgccgc ggggctgcac cgctacctgc gcgacttctg ggctgccac     300
gtggcctggt ccggctctca gctgcgcctg ccgcggccac tgccagccgt gccggggag     360
ctgaccgagg ccacgcccaa caggtaccgc tattaccaga atgtgtgcac gcaaagctac     420
tccttcgtgt ggtgggactg ggcccgctgg gagcgagaga tagactggat ggcgctgaat     480
ggcatcaacc tggcactggc ctggagcggc aggaggcca tctggcagcg ggtgtacctg     540
gccttgggcc tgacccaggc agagatcaat gagttctta ctggtcctgc cttcctggcc     600
tgggggcgaa tgggcaacct gcacacctgg gatggcccc tgccccctc ctggcacatc      660
aagcagcttt acctgcagca ccgggtcctg accagatgc gctccttcgg catgaccca     720
gtgctgcctg cattcgcggg gcatgttccc gaggctgtca ccagggtgtt ccctcaggtc     780
aatgtcacga agatgggcag ttggggccac tttaactgtt cctactcctg ctccttcctt     840
ctggctccgg aagaccccat attccccatc atcgggagct cttcctgcga gagctgatca     900
agagtttgg cacagaccac atctatgggg ccgacacttt caatgagatg cagccacctt     960
cctcagagcc ctcctacctt gccgcagcca ccactgccgt ctatgaggcc atgactgcag    1020
tggatactga ggctgtgtgg ctgctccaag ctggctctt ccagcaccag ccgcagttct    1080
gggggcccgc ccagatcagg gctgtgctgg agctgtgcc ccgtggccgc ctcctggttc    1140
tggacctgtt tgctgagagc cagcctgtgt ataccccgcac tgcctccttc cagggccagc    1200
ccttcatctg gtgcatgctg cacaactttg ggggaaacca tggtcttttt ggagccctag    1260
aggctgtgaa cggaggccca gaagctgccc gcctcttccc caactccacc atggtaggca    1320
cgggcatggc ccccgagggc atcagccaga acgaagtggt ctattccctc atggctgagc    1380
tgggctggcg aaaggaccca gtgccagatt ggcagcctg gtgaccagc tttgccgccc    1440
ggcggtatgg ggtctcccac ccggacgcag gggcagcgtg gaggctactg ctccggagtg    1500
tgtacaactg ctccggggag gcctgcaggg ccacaatcg tagcccgctg gtcaggcggc    1560
cgtccctaca gatgaatacc agcatctggt acaaccgatc tgatgtgttt gaggcctggc    1620
ggctgctgct cacatctgct ccctcctgg ccaccagccc cgccttccgc tacgacctgc    1680
tggacctcac tcggcaggca gtgcaggagc tggtcagctt gtactatgag gaggcaagaa    1740
gcgcctacct gagcaaggag ctggcctccc tgttgagggc tggaggcgtc ctggcctatg    1800
agctgctgcc ggcactggac gaggtgctgg ctagtgacag ccgcttcttg ctgggcagct    1860
ggctagagca ggcccgagca gcggcagtca gtgaggccga ggccgattc tacgagcaga    1920
acagccgcta ccagctgacc ttgtgggggc agaaggcaa catcctggac atatgccaaca    1980
agcagctggc ggggttggtg ccaactact acacccctcg ctggcggctt ttcctggagg    2040
```

```
cgctggttga cagtgtggcc cagggcatcc ctttccaaca gcaccagttt gacaaaaatg    2100
tcttccaact ggagcaggcc ttcgttctca gcaagcagag gtaccccagc cagccgcgag    2160
gagacactgt ggacctggcc aagaagatct tcctcaaata ttaccccgc tgggtggccg     2220 gctcttgg                                                              2228
```

<210> SEQ ID NO 4
<211> LENGTH: 743
<212> TYPE: PRT
<213> ORGANISM: Artificial
<220> FEATURE:
<223> OTHER INFORMATION: NaGlu-IgFII Fusion Construct

<400> SEQUENCE: 4

```
Met Glu Ala Val Ala Val Ala Ala Val Gly Val Leu Leu Leu Ala
1               5                   10                  15

Gly Ala Gly Gly Ala Ala Gly Asp Glu Ala Arg Glu Ala Ala Val
                20                  25                  30

Arg Ala Leu Val Ala Arg Leu Leu Gly Pro Gly Pro Ala Ala Asp Phe
            35                  40                  45

Ser Val Ser Val Glu Arg Ala Leu Ala Ala Lys Pro Gly Leu Asp Thr
50                  55                  60

Tyr Ser Leu Gly Gly Gly Ala Ala Arg Val Arg Val Arg Gly Ser
65                  70                  75              80

Thr Gly Val Ala Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
                100                 105                 110

Pro Leu Pro Ala Val Pro Gly Glu Leu Thr Glu Ala Thr Pro Asn Arg
            115                 120                 125

Tyr Arg Tyr Tyr Gln Asn Val Cys Thr Gln Ser Tyr Ser Phe Val Trp
        130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
        195                 200                 205

Thr Trp Asp Gly Pro Leu Pro Pro Ser Trp His Ile Lys Gln Leu Tyr
    210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
        275                 280                 285

Pro Ile Ile Gly Ser Leu Phe Leu Arg Glu Leu Ile Lys Glu Phe Gly
    290                 295                 300

Thr Asp His Ile Tyr Gly Ala Asp Thr Phe Asn Glu Met Gln Pro Pro
305                 310                 315                 320
```

```
Ser Ser Glu Pro Ser Tyr Leu Ala Ala Ala Thr Thr Ala Val Tyr Glu
            325                 330                 335

Ala Met Thr Ala Val Asp Thr Glu Ala Val Trp Leu Leu Gln Gly Trp
        340                 345                 350

Leu Phe Gln His Gln Pro Gln Phe Trp Gly Pro Ala Gln Ile Arg Ala
            355                 360                 365

Val Leu Gly Ala Val Pro Arg Gly Arg Leu Leu Val Leu Asp Leu Phe
        370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
        435                 440                 445

Ser Gln Asn Glu Val Val Tyr Ser Leu Met Ala Glu Leu Gly Trp Arg
    450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
        515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
    610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
    690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp
```

740

<210> SEQ ID NO 5
<211> LENGTH: 183
<212> TYPE: DNA
<213> ORGANISM: Homo sapiens

<400> SEQUENCE: 5
ctttgcggcg gggagctggt ggacaccctc cagttcgtct gtggggaccg cggcttctac    60
ttcagcaggc ccgcaagccg tgtgagccgt cgcagccgtg gcatcgttga ggagtgctgt   120
ttccgcagct gtgacctggc cctcctggag acgtactgtg ctacccccgc caagtccgag   180
tga                                                                 183

<210> SEQ ID NO 6
<211> LENGTH: 60
<212> TYPE: PRT
<213> ORGANISM: Homo sapiens

<400> SEQUENCE: 6

Leu Cys Gly Gly Glu Leu Val Asp Thr Leu Gln Phe Val Cys Gly Asp
1               5                   10                  15

Arg Gly Phe Tyr Phe Ser Arg Pro Ala Ser Arg Val Ser Arg Arg Ser
                20                  25                  30

Arg Gly Ile Val Glu Glu Cys Cys Phe Arg Ser Cys Asp Leu Ala Leu
            35                  40                  45

Leu Glu Thr Tyr Cys Ala Thr Pro Ala Lys Ser Glu
        50                  55                  60

<210> SEQ ID NO 7
<211> LENGTH: 15
<212> TYPE: PRT
<213> ORGANISM: Artificial
<220> FEATURE:
<223> OTHER INFORMATION: Peptide Linker

<400> SEQUENCE: 7

Gly Gly Gly Gly Gly Ala Ala Ala Ala Ala Gly Gly Gly Gly Gly
1               5                   10                  15

<210> SEQ ID NO 8
<211> LENGTH: 806
<212> TYPE: PRT
<213> ORGANISM: Artificial
<220> FEATURE:
<223> OTHER INFORMATION: NaGlu-IgFII Fusion Construct

<400> SEQUENCE: 8

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
                20                  25                  30

Arg Ala Leu Val Ala Arg Leu Leu Gly Pro Gly Pro Ala Ala Asp Phe
            35                  40                  45

Ser Val Ser Val Glu Arg Ala Leu Ala Ala Lys Pro Gly Leu Asp Thr
        50                  55                  60

Tyr Ser Leu Gly Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
                85                  90                  95

```
Cys Gly Cys His Val Ala Trp Ser Gly Ser Gln Leu Arg Leu Pro Arg
            100                 105                 110

Pro Leu Pro Ala Val Pro Gly Glu Leu Thr Glu Ala Thr Pro Asn Arg
        115                 120                 125

Tyr Arg Tyr Tyr Gln Asn Val Cys Thr Gln Ser Tyr Ser Phe Val Trp
    130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
        195                 200                 205

Thr Trp Asp Gly Pro Leu Pro Pro Ser Trp His Ile Lys Gln Leu Tyr
    210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
        275                 280                 285

Pro Ile Ile Gly Ser Leu Phe Leu Arg Glu Leu Ile Lys Glu Phe Gly
    290                 295                 300

Thr Asp His Ile Tyr Gly Ala Asp Thr Phe Asn Glu Met Gln Pro Pro
305                 310                 315                 320

Ser Ser Glu Pro Ser Tyr Leu Ala Ala Ala Thr Ala Val Tyr Glu
                325                 330                 335

Ala Met Thr Ala Val Asp Thr Glu Ala Val Trp Leu Leu Gln Gly Trp
            340                 345                 350

Leu Phe Gln His Gln Pro Gln Phe Trp Gly Pro Ala Gln Ile Arg Ala
        355                 360                 365

Val Leu Gly Ala Val Pro Arg Gly Arg Leu Leu Val Leu Asp Leu Phe
    370                 375                 380

Ala Glu Ser Gln Pro Val Tyr Thr Arg Thr Ala Ser Phe Gln Gly Gln
385                 390                 395                 400

Pro Phe Ile Trp Cys Met Leu His Asn Phe Gly Gly Asn His Gly Leu
                405                 410                 415

Phe Gly Ala Leu Glu Ala Val Asn Gly Gly Pro Glu Ala Ala Arg Leu
            420                 425                 430

Phe Pro Asn Ser Thr Met Val Gly Thr Gly Met Ala Pro Glu Gly Ile
        435                 440                 445

Ser Gln Asn Glu Val Val Tyr Ser Leu Met Ala Glu Leu Gly Trp Arg
    450                 455                 460

Lys Asp Pro Val Pro Asp Leu Ala Ala Trp Val Thr Ser Phe Ala Ala
465                 470                 475                 480

Arg Arg Tyr Gly Val Ser His Pro Asp Ala Gly Ala Ala Trp Arg Leu
                485                 490                 495

Leu Leu Arg Ser Val Tyr Asn Cys Ser Gly Glu Ala Cys Arg Gly His
            500                 505                 510

Asn Arg Ser Pro Leu Val Arg Arg Pro Ser Leu Gln Met Asn Thr Ser
```

```
            515                 520                 525
Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
        595                 600                 605

Val Leu Ala Ser Asp Ser Arg Phe Leu Leu Gly Ser Trp Leu Glu Gln
610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp Gly Ala Pro Leu Cys Gly Gly Glu Leu
            740                 745                 750

Val Asp Thr Leu Gln Phe Val Cys Gly Asp Arg Gly Phe Tyr Phe Ser
        755                 760                 765

Arg Pro Ala Ser Arg Val Ser Arg Arg Ser Arg Gly Ile Val Glu Glu
770                 775                 780

Cys Cys Phe Arg Ser Cys Asp Leu Ala Leu Leu Glu Thr Tyr Cys Ala
785                 790                 795                 800

Thr Pro Ala Lys Ser Glu
                805

<210> SEQ ID NO 9
<211> LENGTH: 860
<212> TYPE: PRT
<213> ORGANISM: Artificial
<220> FEATURE:
<223> OTHER INFORMATION: NaGlu-IgFII Fusion Construct

<400> SEQUENCE: 9

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
            20                  25                  30

Arg Ala Leu Val Ala Arg Leu Leu Gly Pro Gly Pro Ala Ala Asp Phe
        35                  40                  45

Ser Val Ser Val Glu Arg Ala Leu Ala Ala Lys Pro Gly Leu Asp Thr
    50                  55                  60

Tyr Ser Leu Gly Gly Gly Gly Ala Ala Arg Val Arg Val Arg Gly Ser
```

```
                65                  70                  75                  80
        Thr Gly Val Ala Ala Ala Gly Leu His Arg Tyr Leu Arg Asp Phe
                        85                  90                  95
        Cys Gly Cys His Val Ala Trp Ser Gly Ser Gln Leu Arg Leu Pro Arg
                       100                 105                 110
        Pro Leu Pro Ala Val Pro Gly Glu Leu Thr Glu Ala Thr Pro Asn Arg
                       115                 120                 125
        Tyr Arg Tyr Tyr Gln Asn Val Cys Thr Gln Ser Tyr Ser Phe Val Trp
                       130                 135                 140
        Trp Asp Trp Ala Arg Trp Glu Arg Glu Ile Asp Trp Met Ala Leu Asn
        145                 150                 155                 160
        Gly Ile Asn Leu Ala Leu Ala Trp Ser Gly Gln Ala Ile Trp Gln
                       165                 170                 175
        Arg Val Tyr Leu Ala Leu Gly Leu Thr Gln Ala Glu Ile Asn Glu Phe
                       180                 185                 190
        Phe Thr Gly Pro Ala Phe Leu Ala Trp Gly Arg Met Gly Asn Leu His
                       195                 200                 205
        Thr Trp Asp Gly Pro Leu Pro Pro Ser Trp His Ile Lys Gln Leu Tyr
        210                 215                 220
        Leu Gln His Arg Val Leu Asp Gln Met Arg Ser Phe Gly Met Thr Pro
        225                 230                 235                 240
        Val Leu Pro Ala Phe Ala Gly His Val Pro Glu Ala Val Thr Arg Val
                       245                 250                 255
        Phe Pro Gln Val Asn Val Thr Lys Met Gly Ser Trp Gly His Phe Asn
                       260                 265                 270
        Cys Ser Tyr Ser Cys Ser Phe Leu Leu Ala Pro Glu Asp Pro Ile Phe
                       275                 280                 285
        Pro Ile Ile Gly Ser Leu Phe Leu Arg Glu Leu Ile Lys Glu Phe Gly
                       290                 295                 300
        Thr Asp His Ile Tyr Gly Ala Asp Thr Phe Asn Glu Met Gln Pro Pro
        305                 310                 315                 320
        Ser Ser Glu Pro Ser Tyr Leu Ala Ala Ala Thr Thr Ala Val Tyr Glu
                       325                 330                 335
        Ala Met Thr Ala Val Asp Thr Glu Ala Val Trp Leu Leu Gln Gly Trp
                       340                 345                 350
        Leu Phe Gln His Gln Pro Gln Phe Trp Gly Pro Ala Gln Ile Arg Ala
                       355                 360                 365
        Val Leu Gly Ala Val Pro Arg Gly Arg Leu Leu Val Leu Asp Leu Phe
                       370                 375                 380
        Ala Glu Ser Gln Pro Val Tyr Thr Arg Thr Ala Ser Phe Gln Gly Gln
        385                 390                 395                 400
        Pro Phe Ile Trp Cys Met Leu His Asn Phe Gly Asn His Gly Leu
                       405                 410                 415
        Phe Gly Ala Leu Glu Ala Val Asn Gly Gly Pro Glu Ala Ala Arg Leu
                       420                 425                 430
        Phe Pro Asn Ser Thr Met Val Gly Thr Gly Met Ala Pro Glu Gly Ile
                       435                 440                 445
        Ser Gln Asn Glu Val Val Tyr Ser Leu Met Ala Glu Leu Gly Trp Arg
                       450                 455                 460
        Lys Asp Pro Val Pro Asp Leu Ala Ala Trp Val Thr Ser Phe Ala Ala
        465                 470                 475                 480
        Arg Arg Tyr Gly Val Ser His Pro Asp Ala Gly Ala Ala Trp Arg Leu
                       485                 490                 495
```

Leu Leu Arg Ser Val Tyr Asn Cys Ser Gly Glu Ala Cys Arg Gly His
            500                 505                 510

Asn Arg Ser Pro Leu Val Arg Pro Ser Leu Gln Met Asn Thr Ser
            515                 520                 525

Ile Trp Tyr Asn Arg Ser Asp Val Phe Glu Ala Trp Arg Leu Leu Leu
530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Leu Pro Ala Leu Asp Glu
            595                 600                 605

Val Leu Ala Ser Asp Ser Arg Phe Leu Leu Gly Ser Trp Leu Glu Gln
610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
            675                 680                 685

Gly Ile Pro Phe Gln Gln His Gln Phe Asp Lys Asn Val Phe Gln Leu
690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp Gly Ala Pro Gly Gly Gly Gly Ala
            740                 745                 750

Ala Ala Ala Ala Gly Gly Gly Gly Gly Ala Pro Gly Gly Gly Gly
            755                 760                 765

Gly Ala Ala Ala Ala Gly Gly Gly Gly Ala Pro Gly Gly
            770                 775                 780

Gly Gly Gly Ala Ala Ala Ala Gly Gly Gly Gly Ala Pro
785                 790                 795                 800

Leu Cys Gly Gly Glu Leu Val Asp Thr Leu Gln Phe Val Cys Gly Asp
            805                 810                 815

Arg Gly Phe Tyr Phe Ser Arg Pro Ala Ser Arg Val Ser Arg Arg Ser
            820                 825                 830

Arg Gly Ile Val Glu Glu Cys Cys Phe Arg Ser Cys Asp Leu Ala Leu
            835                 840                 845

Leu Glu Thr Tyr Cys Ala Thr Pro Ala Lys Ser Glu
            850                 855                 860

<210> SEQ ID NO 10
<211> LENGTH: 15
<212> TYPE: PRT
<213> ORGANISM: Artificial
<220> FEATURE:
<223> OTHER INFORMATION: Peptide Linker

<400> SEQUENCE: 10

-continued

```
Gly Gly Gly Gly Gly Ser Ser Ser Ser Ser Gly Gly Gly Gly Gly
1               5                   10                  15

<210> SEQ ID NO 11
<211> LENGTH: 3
<212> TYPE: PRT
<213> ORGANISM: Artificial
<220> FEATURE:
<223> OTHER INFORMATION: Peptide Linker

<400> SEQUENCE: 11

Gly Ala Pro
1

<210> SEQ ID NO 12
<211> LENGTH: 6
<212> TYPE: PRT
<213> ORGANISM: Artificial
<220> FEATURE:
<223> OTHER INFORMATION: Peptide Linker

<400> SEQUENCE: 12

Gly Gly Gly Gly Gly Pro
1               5
```

PEPTIDE LINKERS FOR POLYPEPTIDE COMPOSITIONS AND METHODS FOR USING SAME

RELATED APPLICATIONS

This application is a continuation of U.S. application Ser. No. 13/411,287, now issued as U.S. Pat. No. 8,580,922, filed on Mar. 2, 2012, which claims the benefit of U.S. Provisional Application No. 61/449,225 filed on Mar. 4, 2011, and is a continuation-in-part of U.S. application Ser. No. 13/168,969, now abandoned, filed on Jun. 25, 2011 and International Application No. PCT/US2011/041928 filed on Jun. 25, 2011, the entire teachings of which are incorporated herein by reference.

FIELD OF THE INVENTION

The present inventions are directed to novel peptide linkers and polypeptide compositions comprising such linkers (e.g., chimeric polypeptides) and methods of using and preparing the same.

BACKGROUND OF THE INVENTION

Lysosomal storage disorders represent a group of more than forty rare and inherited metabolic disorders caused by the deficiency or inactivity of specific lysosomal enzymes. In particular, lysosomal storage disorders are caused by the deficiency or inactivity of the lysosomal enzymes which catalyze the stepwise metabolism of lipids or complex glycoproteins known as glycosaminoglycans. As a result of this metabolic deficiency, metabolic precursors progressively accumulate in the cells, tissues and, in particular, the cellular lysosomes of affected subjects. This protein accumulation causes a permanent, progressive cellular damage which affects the appearance, physical abilities, organ and system functioning and, in most cases, the mental development of affected subjects. Although the enzyme deficiencies affect every tissue, a patient's clinical expression may frequently vary depending, for example, on the degree of enzyme deficiency or impairment. The lysosomal storage disorder may also be associated with some degree of neuronal cell loss, predominantly resulting in neurological symptoms, including, mental retardation, severe motor impairments, physical disability, a decreased lifespan and/or combinations of the foregoing.

There are no cures for the lysosomal storage disorders, and treatment is often palliative, offered to subjects primarily to improve their quality of life. Enzyme replacement therapy (ERT) has been a useful therapeutic option for subjects with lysosome storage disorders. ERT generally involves the parenteral administration of natural or recombinantly-derived proteins and/or enzymes to a patient. Approved therapies are administered to patients intravenously and are generally effective in treating the somatic or peripheral symptoms of the underlying enzyme deficiency. To effectively treat lysosomal storage disorders, the administered therapeutic agent (e.g., the deficient lysosomal enzyme) must distribute into the affected cells and tissues after being infused into a patient's bloodstream.

To achieve distribution of the requisite enzymes into affected cells and tissues, the enzymes are generally targeted to specific cell-surface receptors that transport the enzymes into the cells through receptor-mediated endocytosis. For example, in Gaucher's disease, the deficient enzyme, glucocerebrosidase, is targeted to the appropriate cells through the binding of exposed mannose residues on the enzyme to the mannose receptor, which is abundantly expressed on target cells (reticuloendotheilial cells). In cells that lack the mannose receptor, use of the insulin-like growth factor/cation-independent mannose-6-phosphate receptor (IGF-II/CI-MPR) has been proposed for delivery of deficient lysozymes to cells (Kornfeld, S., 1987 Biochem Soc Trans 18:367-374). The IGF-II/CI-MPR receptor is present on the surface of many mammalian cell types and thus provides a means by which to target proteins containing the receptor ligand (e.g., IGFII or mannose-6 phosphate) to a wide variety of cells and tissues, including the central nervous system. However, despite some knowledge of how to target missing lysosomal enzymes to appropriate tissues, there are still no effective therapies for many lysosomal storage disorders (e.g., Sanfilippo syndrome, Farber's disease, and the like). Thus, there remains a need in the art for compositions, particularly compositions that can be administered parenterally, and methods useful for directing agents to the necessary tissues to treat diseases (e.g., lysosomal storage diseases).

SUMMARY OF THE INVENTION

There is a need for compositions and methods that facilitate the transport and delivery of functional therapeutic agents (e.g., proteins, polypeptides) to the desired tissues. Such compositions and methods may be useful in the treatment of a number of diseases or disorders and, in particular, in the treatment of lysosomal storage disorders, like Sanfilippo disease.

Described herein are novel compositions comprising peptide linkers, polypeptide compositions comprising polypeptides joined by the peptide linkers and related polynucleotides, vectors, cells and pharmaceutical compositions. Described linker sequences operably join two peptides/polypeptides of interest such that the expression and activity (e.g., receptor binding and/or enzyme activity) of the polypeptides connected by the linkers are durable and optimal. The polypeptide compositions comprising the peptide linkers facilitate the targeted delivery of polypeptides/proteins of interest to particular cells and/or tissues.

Accordingly, an embodiment of the invention provides for a polypeptide composition comprising a first peptide/polypeptide, a second peptide/polypeptide and a linker comprising one or more sequential or tandem repeats of the amino acid sequence of SEQ ID NO. 1 (GAPGGGG-GAAAAAGGGGG) disposed between the first peptide and the second peptide. In some embodiments, the linker of the polypeptide composition comprises three sequential or tandem repeats of SEQ ID NO. 1 and, in some embodiments, the linkers further comprise the amino acid sequence glycine alanine proline (GAP) at the 3' end of SEQ ID NO. 1. In other embodiments, one or more alanine residues of the linkers can be substituted with one or more serine residues. In certain embodiments, the first peptide of the polypeptide composition comprises the amino acid sequence of SEQ ID NO. 4. In still other embodiments the second peptide comprises a receptor binding domain and, in further embodiments, the second peptide comprises the amino acid sequence of SEQ ID NO. 6.

In certain embodiments, a polypeptide composition comprises a first peptide comprising the amino acid sequence of SEQ ID NO. 4; a second peptide comprising the amino acid sequence of SEQ ID NO. 6; and a linker comprising one or more sequential or tandem repeats of the amino acid sequence of SEQ ID NO. 1 disposed between the first peptide and the second peptide. In some embodiments, the linker comprises three sequential repeats of SEQ ID NO. 1. In other embodiments, the linkers can further comprise the amino acid sequence glycine alanine proline (GAP) at the 3' end of the SEQ ID NO. 1. In still other embodiments, one or more alanine residues of the linkers are substituted with one or more serine residues.

In some embodiments, a polypeptide composition comprises a first peptide comprising the amino acid sequence of SEQ ID NO. 4; a second peptide comprising the amino acid sequence of SEQ ID NO. 6; and a linker comprising the amino acid sequence of SEQ ID NO. 2 disposed between the first peptide and second peptide. In certain embodiments, one or more alanine residues of the linker are substituted with one or more serine residues.

The invention also provides for peptide/polypeptide linkers which are described herein. For example, in some embodiments, a polypeptide linker comprises 18 contiguous amino acid residues, wherein the linker comprises 1 proline residue within the first five amino acid residues of the linker and 17 amino acid residues selected from the group consisting of one or more glycine residues and one or more alanine residues. In other embodiments, the 3' end of the polypeptide linker further comprises three contiguous amino acids comprising 1 proline residue and two amino acid residues selected from the group consisting of glycine and alanine. In some embodiments, one or more alanine residues of the linker are substituted with one or more serine residues.

In some embodiments, a polypeptide linker comprises 21 contiguous amino acid residues wherein the linker comprises a first proline residue that is within the first five amino acid residues of the linker; 19 amino acid residues selected from the group consisting of one or more glycine residues and one or more alanine residues; and a second proline residue that is within the last five amino acids of the linker.

In certain embodiments, one or more alanine residues of the linkers are substituted with one or more serine residues. In still other embodiments, the polypeptide linkers comprise two times as many glycine and serine residues as alanine residues.

In some embodiments, the polypeptide linker consists of the amino acid sequence of SEQ ID NO. 7 (GGGG-GAAAAAGGGGG).

In other embodiments, the invention provides for polypeptide linker compositions that comprise one or more sequential repeats of a polypeptide linker consisting of the amino acid sequence of SEQ ID NO. 7. In other embodiments, the 5' end of the polypeptide linker composition further comprises three contiguous amino acids comprising one proline residue and two amino acid residues selected from the group consisting of glycine and alanine.

In still other embodiments, a polypeptide linker consists of the amino acid sequence of SEQ ID NO. 1. In certain embodiments, the invention provides for a polypeptide linker composition comprising one or more sequential repeats of a polypeptide linker consisting of SEQ ID NO. 1.

In further embodiments, the 3' end of the above polypeptide linker compositions further comprises three contiguous amino acids comprising one proline residue and two amino acid residues selected from the group consisting of glycine and alanine. In certain embodiments, the three contiguous amino acid residues comprise the amino acid sequence glycine alanine proline (GAP).

In some embodiments, the polypeptide linker consists of the amino acid sequence of SEQ ID NO. 2 (GAPGGGG-GAAAAAGGGGGAPGGGG-GAAAAAGGGGGAPGGGGGAAAAAGGGGGAP).

In certain embodiments, the invention provides for a polypeptide composition comprising a first peptide; a second peptide; and a polypeptide linker disposed between the first peptide and the second peptide, wherein the linker comprises any of the aforementioned polypeptide linkers or polypeptide linker compositions.

In other embodiments, the invention also provides for polynucleotides that encode the polypeptide linkers and/or polypeptide compositions described herein. Thus, some embodiments provide a polynucleotide encoding a polypeptide comprising the amino acid sequence of SEQ ID NO. 1; SEQ ID NO. 2; or one or more sequential repeats of SEQ ID NO. 1. In some embodiments, one or more alanine residues of the polypeptide are substituted with one or more serine residues and the polynucleotide encodes for the one or more substituted serine residues.

In other embodiments, a polynucleotide encodes a polypeptide composition comprising the amino acid sequence of a first peptide; a second peptide; and a linker comprising one or more sequential repeats of the amino acid sequence of SEQ ID NO. 1 disposed between the first peptide and the second peptide. In certain embodiments, the linker of the polypeptide composition comprises three sequential or tandem repeats of SEQ ID NO. 1. In still other embodiments, one or more alanine residues of the linker of the polypeptide compositions are substituted with one or more serine residues, and the polynucleotide encodes the one or more substituted serine residues. In further embodiments of the foregoing polynucleotides, the 3' end of the linker of the polypeptide compositions further comprises the amino acid sequence glycine alanine proline (GAP), and the polynucleotide encodes the GAP amino acid sequence.

In certain embodiments, a polynucleotide encodes a first peptide of the polypeptide composition that comprises the amino acid sequence of SEQ ID NO. 4. In other embodiments, the polynucleotide encodes a second peptide of the polypeptide composition that comprises a receptor binding domain and, in some embodiments, the second peptide comprises the amino acid sequence of SEQ ID NO. 6.

Also described herein are expression vectors comprising the aforementioned polynucleotides which encode the polypeptide compositions described herein. Other embodiments described herein relate to recombinant cells comprising the foregoing polynucleotides and expression vectors.

In addition, the invention provides for pharmaceutical compositions comprising the polypeptide compositions described herein and a pharmaceutically acceptable carrier. For example, in some embodiments, the pharmaceutical composition comprises polypeptide compositions comprising a first peptide comprising the amino acid sequence of SEQ ID NO. 4 and a second peptide comprising the amino acid sequence of SEQ ID NO. 6. In some of these embodiments, the linker disposed between the first peptide and second peptide comprises one or more sequential or tandem repeats of SEQ ID NO. 1 (e.g., one, two, three, four, five, six, seven, eight, nine, ten or more sequential or tandem repeats of SEQ ID NO. 1), and in other of these embodiments, the linker comprises the amino acid sequence of SEQ ID NO. 2.

In certain embodiments, the invention also provides for pharmaceutical compositions comprising the polynucleotides described herein and a pharmaceutically acceptable carrier. The invention further provides for pharmaceutical compositions comprising the recombinant cells described herein and a pharmaceutically acceptable carrier.

Also described herein are methods of producing a polypeptide composition, the method comprising culturing the recombinant cells described herein under conditions suitable for the expression of the polypeptide.

Methods of delivering a therapeutic polypeptide to a subject in need thereof are also described herein. Thus, some embodiments disclosed herein are methods of delivering a therapeutic polypeptide to a subject in need thereof comprising administering to the subject any of the aforementioned polypeptide compositions described herein.

In other embodiments, a method of delivering a therapeutic polypeptide to a subject in need thereof comprises administering to the subject a polypeptide composition comprising a first peptide comprising the amino acid sequence of SEQ ID NO. 4; a second peptide comprising the amino acid sequence of SEQ ID NO. 6; and a linker comprising one or more sequential repeats of the amino acid sequence of SEQ ID NO. 1 disposed between the first peptide and the second peptide. In other embodiments of the method, the linker further comprises GAP at the 3' end of SEQ ID NO. 1. In certain embodiments of the method, the linker comprises the amino acid sequence of SEQ ID NO. 2. In still other embodiments of the methods, one or more alanine residues of the linkers are substituted with one or more serine residues.

In some embodiments, a method of delivering a therapeutic polypeptide to a subject in need thereof comprises administering to the subject one or more of the above-mentioned expression vectors described herein. Certain other embodiments relate to methods of delivering a therapeutic polypeptide to a subject in need thereof comprising administering to the subject one or more of the aforementioned recombinant cells described herein.

Also described herein are methods of treating a lysosomal storage disease, the method comprising, in some embodiments, administering to a subject in need thereof an effective amount of any one or the aforementioned pharmaceutical compositions described herein (comprising e.g., polypeptide compositions, polynucleotides and/or host cells described herein). In certain embodiments, the lysosomal storage disease is Sanfilippo syndrome.

Still other embodiments described herein relate to methods of treating Sanfilippo syndrome. In some embodiments, the method comprises administering to a patient in need thereof an effective amount of the aforementioned pharmaceutical compositions described herein.

In other embodiments, a method of treating Sanfilippo syndrome comprises administering to a patient in need thereof an effective amount of a pharmaceutical composition comprising a first peptide comprising the amino acid sequence of SEQ ID NO. 4; a second peptide comprising the amino acid sequence of SEQ ID NO. 6; and a linker comprising one or more sequential repeats of SEQ ID NO. 1 disposed between the first peptide and the second peptide. In certain embodiments of the method, the linker further comprises the amino acid sequence gap at the 3' end of SEQ ID NO. 1. In other embodiments of the method, the linker comprises the amino acid sequence of SEQ ID NO. 2.

In certain embodiments of the methods, the pharmaceutical compositions are administered parenterally.

The above discussed and many other features and attendant advantages of the present invention will become better understood by reference to the following detailed description of the invention when taken in conjunction with the accompanying examples. The various embodiments described herein are complimentary and can be combined or used together in a manner understood by the skilled person in view of the teachings contained herein.

BRIEF DESCRIPTION OF THE DRAWINGS

FIG. 1 illustrates the amino acid sequence of a peptide linker comprising a glycine alanine proline (GAP) sequence joined to a glycine alanine glycine (GAG) repeat sequence (SEQ ID NO. 1).

FIG. 2 illustrates the amino acid sequence of a peptide linker comprising three sequential or tandem repeats of SEQ ID NO. 1 joined at the 3' end to a GAP sequence (SEQ ID NO. 2).

FIG. 4A illustrates the nucleotide sequence of human NaGlu (SEQ ID NO. 3). FIG. 4B illustrates the amino acid sequence of human NaGlu (SEQ ID NO. 4).

FIG. 5A illustrates the nucleotide sequence of human IGFII (SEQ ID NO. 5) FIG. 5B illustrates the amino acid sequence of human IGFII (SEQ ID NO. 6).

Figure 6:
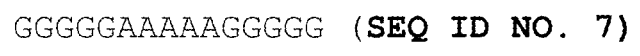

FIG. 6 illustrates the amino acid sequence of a peptide linker comprising a GAG repeat sequence (SEQ ID NO. 7).

FIG. 7 illustrates the amino acid sequence of the NaGlu-IGFII construct illustrated in FIG. 3A (SEQ ID NO. 8).

FIG. 8 illustrates the amino acid sequence of the NaGlu-IGFII construct illustrated in FIG. 3B (SEQ ID NO. 9).

Figure 12:
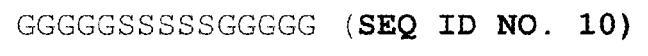

FIG. 12 illustrates the amino acid sequence of a peptide linker (SEQ ID NO. 10).

Figure 13:
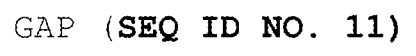

FIG. 13 illustrates the amino acid sequence of a peptide linker (SEQ ID NO. 11).

Figure 14:
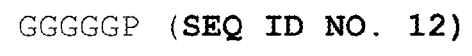

FIG. 14 illustrates the amino acid sequence of a peptide linker (SEQ ID NO. 12).

DETAILED DESCRIPTION OF THE INVENTION

Figure 3A:
FIG. 3A illustrates the α-N-acetylglucosaminidase-insulin-like growth factor (NaGlu-IGFII) construct joined by a GAP linker.

Compositions are described herein that provide a means to make (e.g., design, engineer) chimeric or fusion polypeptides. The polypeptide compositions can also provide means of facilitating the delivery of agents (e.g., polypeptides/peptides, proteins and/or enzymes) to cells, tissues or organs of interest. In particular, the compositions and methods can be used to selectively deliver agents to an appropriate tissue of a subject in need thereof, thereby treating a disease or disorder. These therapeutic compositions can be polynucleotides or polypeptides that comprise a therapeutic agent (e.g., protein/enzyme) joined to a targeting agent (e.g., cell receptor ligand protein) by a linker sequence that allows for the proper expression, folding and activity of the therapeutic and/or targeting agent. In some aspects, the therapeutic composition comprises a lysosomal protein or enzyme connected by the linker sequence to a cell-surface receptor ligand protein. The therapeutic polypeptide composition can be used to treat disorders such as lysosomal storage diseases.

As used herein, the phrase "lysosomal storage disorder" or lysosomal storage disease" refers to a class of inherited diseases related to the aberrant expression of or deficiency of one or more lysosomal enzymes. These enzyme deficiencies result in detrimental accumulation of metabolic products in the lysosomes of affected subjects. Representative lysosomal storage disorders include aspartylglucosaminuria, cholesteryl ester storage disease, cystinosis, Danon disease, Fabry disease, Farber's disease, fucosidosis, falactosialidosis types I/II, Gaucher disease types 1, 2, 3, globoid cell leucodystrophy/Krabbe disease, glycogen storage disease II/Pompe disease, GM1-gangliosidosis types I/III, GM2-gangliosidosis type I/Tay-Sachs disease, GM2-gangliosidosis type II/Sandhoff disease, α-mannosidosis types I/II, β-mannosidosis, metachromatic leukodystrophy (MLD), mucolipidosis type I/sialidosis types I/II, mucolipidosis types mucolipidosis type III pseudo-Hurler polydystrophy, mucopolysaccharidosis (e.g. types I, II, IIIA, IIIB, IIIC, IIID, IVA, IVB, VI, VII and IX), multiple sulphatase deficiency, neuronal ceroid lipofuscinosis (e.g. Batten, infantile, late infantile and adult), Niemann-Pick disease (e.g. types A, B, C1, C2), Schindler disease types I/II, sialic acid storage disease, Sanfilippo disease, and Wolman's disease (acid lipase deficiency). In one aspect of the invention, the compositions comprise a therapeutic agent whose deficiency is linked to a lysosomal storage disorder.

Polypeptide composition and polynucleotides encoding the polypeptide compositions are described herein, in which the polypeptide compositions comprise a first and second peptide/polypeptide, connected by a linker sequence disclosed herein. The inventors have surprisingly found that a linker comprising one or more sequential or tandem repeats of SEQ ID NO. 1 (GAPGGGGGAAAAAGGGGG), connecting two protein sequences (e.g., a first polypeptide and a second polypeptide) results in the production of a polypeptide that is well-expressed and highly active (e.g., biologically active). As used herein, the term "polypeptide" or "peptide" refers a polymer of amino acid residues typically joined exclusively by peptide bonds, that can be produced naturally (e.g., isolated, essentially purified or purified) or synthetically (e.g., by chemical synthesis). A polypeptide produced by expression of a non-host DNA molecule is a "heterologous" peptide or polypeptide. An "amino acid residue" comprising the polypeptide can be a natural or non-natural amino acid residue linked by peptide bonds and/or bonds different from peptide bonds. The amino acid residues can be in D-configuration or L-configuration. In some aspects, the polypeptides referred to herein are proteins, peptides or fragments thereof produced by the expression of recombinant nucleic acid. In some embodiments, the polypeptide compositions described herein comprise two polypeptides connected by a linker sequence (e.g., SEQ ID NO. 2), in which one of the two polypeptides is a peptide that can be administered to treat a disease or a disorder (e.g., a therapeutic peptide) and the other polypeptide is peptide that can be used to deliver a therapeutic peptide to a target cell, tissue or organ (e.g., a targeting peptide).

The linker or polypeptide linker described herein refers to a peptide sequence designed to connect (e.g., join, link) two protein sequences, wherein the linker peptide sequence is typically not disposed between the two protein sequences in nature. In the context of the present invention, the phrase "linked" or "joined" or "connected" generally refers to a functional linkage between two contiguous or adjacent amino acid sequences to produce a polypeptide that generally does not exist in nature. In certain embodiments, linkage may be used to refer to a covalent linkage of, for example, the amino acid sequences of the one or more therapeutic peptide agents and the one or more targeting agents (e.g., binding or receptor ligand peptides). Generally, linked proteins are contiguous or adjacent to one another and retain their respective operability and function when joined. Peptides comprising the chimeric polypeptides disclosed herein are linked by means of an interposed peptide linker comprising one or more amino acids.

Such linkers may provide desirable flexibility to permit the desired expression, activity and/or conformational positioning of the chimeric polypeptide. A typical amino acid linker is generally designed to be flexible or to interpose a structure, such as an alpha-helix, between the two protein moieties. A linker can be fused to the N-terminus or C-terminus of a polypeptide encoding a lysosomal enzyme, or inserted internally. A linker is also referred to as a spacer.

The linker peptide sequence can be of any appropriate length to connect one or more proteins of interest and is preferably designed to be sufficiently flexible so as to allow the proper folding and/or function and/or activity of one or both of the peptides it connects. Thus, the linker peptide can have a length of no more than 3, no more than 5, no more than 10, no more than 15, no more than 20, no more than 25, no more than 30, no more than 35, no more than 40, no more than 45, no more than 50, no more than 55, no more than 60, no more than 65, no more than 70, no more than 75, no more than 80, no more than 85, no more than 90, no more than 95 or no more than 100 amino acids. In some embodiments, the linker peptide can have a length of at least 3, at least 4, at least 5, at least 6, at least 7, at least 8, at least 9, at least 10, at least 12, at least 15, at least 18, at least 20, at least 25, at least 30, at least 35, at least 40, at least 45, or at least 50 amino acids. In some embodiments, the linker comprises at least 10 and no more than 60 amino acids, at least 10 and no more than 55 amino acids, at least 10 and no more than 50 amino acids, at least 10 and no more than 45 amino acids, at least 10 and no more than 40 amino acids, at least 10 and no more 35 amino acids, at least 10 and no more than 30 amino acids, at least 10 and no more than 25 amino acids, at least 10 and no more than 20 amino acids or at least 10 and no more than 15 amino acids. In certain embodiments, the linker comprises 12 to 57 amino acids, and in particular embodiments, comprises 57 amino acids. In a polypeptide composition comprising a linker, the 5' end (e.g., terminus) of the linker peptide sequence (e.g., amino acid sequence) is adjacent to and covalently linked to the 3' end of one protein sequence (e.g., full-length protein or protein domain, fragment or variant) and, further, the 3' end of the linker amino acid sequence is adjacent to and covalently linked to the 5' end of another protein sequence. Polypeptide compositions produced in this manner are commonly referred to a fusion or chimeric protein/polypeptides and typically are made by the expression (e.g., transcription, translation) of nucleic acid sequences encoding the polypeptide compositions, in the appropriate system. Means by which to make fusion and/or chimeric polypeptides are well-known in the art (see for example, Sambrook et al., Molecular Cloning: A Laboratory Manual, Cold Springs Harbor Laboratory, 1992) New York which is incorporated by reference herein in its entirety).

In certain embodiments, the linker amino acid sequence is comprised of glycine, alanine and/or serine amino acid residues. The inventors have discovered that simple amino acids (e.g., amino acids with simple side chains (e.g., H, $CH_3$ or $CH_2OH$) and/or unbranched) are advantageous for use in a peptide linker as the lack of branched side chains on these amino acids provides greater flexibility (e.g., two-dimensional or three-dimensional flexibility) within the linker and, accordingly, within a polypeptide composition. Further, the inventors have found that alternating the glycine, alanine and/or serine residues provides even more order and greater flexibility with in the linker. The amino acids can alternate/repeat in any manner consistent with the linker remaining functional (e.g., resulting in expressed and/or active polypeptide(s)). In any of the linkers, the alanine amino acid residues can be substituted with serines. Thus, the amino acids in the liker can repeat every one (e.g., GAGA, GSGS), every two (e.g., GGAAGGAA, GGSSGGSS), every three, every four, every five, every 6, every 7, every 8, every 9 or every 10 or more amino acids, or the amino acids can repeat in any combination of the foregoing. In certain embodiments, the amino acids repeat every five amino acids and the linker consists of one or more glycine alanine glycine repeats. For example, the peptide linker can consist of a GGGG-GAAAAAGGGGG (SEQ ID NO. 7) or GGGGGSSSSSGGGGG (SEQ ID NO: 10) repeat.

In addition, the inventors have discovered that placing a proline residue within the first (e.g., 5' end) and/or last (e.g., 3' end) five amino acids of the linker provides for additional benefit within the linker. For example, a linker or spacer can be GAP (SEQ ID NO. 11) or GGGGGP (SEQ ID NO. 12). Not to be bound by theory, it is believed that, unlike glycine, alanine and serine which are flexible amino acids, proline, whose cyclic side chain results in inflexibility, may result in a kink near the end(s) of the otherwise flexible linker, and thereby keep the polypeptides connected by the linker appropriately separated. Thus, the linker amino acid sequence can have a proline in the first, second, third, fourth or fifth amino acid residue and/or a proline within the last, second to last, third to last, fourth to last or fifth to last amino acid residue within the linker. In certain embodiments, the peptide linker can comprise 18 contiguous amino acid residues in which one of the amino acid residues is a proline that is located at any one of the first five amino residues of the linker, and the remaining 17 amino acid residues are comprised of glycine and alanine residues (e.g., one or more glycine and one or more alanine residues). The glycine and alanine amino acid residues of the linker can comprise any combination of glycine and alanine residues, including the aforementioned glycine alanine glycine repeats. The linker can further comprise three contiguous amino acids comprising a second proline, a glycine residue and/or an alanine residue, to produce a peptide linker comprising 21 amino acids. The second proline may also be any one of the last five amino acids in the linker amino acid sequence.

The foregoing peptide linkers can be flanked by one or more amino acid sequences that are encoded by a desired restriction endonuclease site or sites. Numerous endonuclease cleavage sites (e.g., EcoRI, BamHI, HindIII, AscI sites and the like) are well-known in the art, and the selection of which cleavage sites to include in the linker (and/or polypeptide(s)) nucleic acid sequence is best determined by the skilled artisan, the site generally being chosen with regard to the respective nucleic acid sequences being linked. The endonuclease restriction sites can be the same site on each end of the linker sequence or different restriction sites as needed and/or desired. In some embodiments, the glycine alanine glycine amino acid repeats of the linker are flanked by glycine alanine proline (GAP) amino acid sequences at the 5' and/or 3' end of the linker amino acid sequence (e.g., SEQ ID NO. 2). The GAP sequence in this instance is encoded for by nucleic acid sequence that represents an AscI restriction endonuclease site. In some embodiments, the linker amino acid sequence comprises SEQ ID NO. 1 (GAPGGGG-GAAAAAGGGGG). In other embodiments, the linker amino acid sequence comprises one or more (e.g., 1, 2, 3, 4 or more) sequential repeats of SEQ ID NO. 1. The inventors have discovered that even one repeat of SEQ ID NO. 1 improves the linker functionality with three and four repeats of SEQ ID NO. 1 being most effective in allowing expression and/or activity of the linked polypeptides. In certain embodiments, the one or more sequential repeats of SEQ ID NO. 1 are further comprised of a gap sequence at the 3' end/terminus of the linker's amino acid sequence. In some embodiments, the linker amino acid sequence comprises SEQ ID NO. 2 (GAPGGGGGAAAAAGGGGGGAPGGGG-GAAAAAGGGGGAPGGGGGAAAAAGGGGGAP).

In some embodiments, a suitable linker or spacer may contain a sequence at least 50%, 55%, 60%, 65%, 70%, 75%, 80%, 85%, 90%, 95%, 98%, or 99% identical to the sequence of SEQ ID NO. 2.

In the polypeptide compositions described herein, the two polypeptides (e.g., a first polypeptide and a second polypeptide) can be recombinantly joined by any of the linker polypeptides described above, with the linker disposed between the two polypeptides. For example, in certain embodiments, the polypeptides or compositions comprise a first and a second polypeptide recombinantly joined by a linker comprising SEQ ID NO. 1 or SEQ ID NO. 2. The two polypeptides can be any amino acid sequences including full-length proteins, protein fragments or portions, functional protein fragments or portions, functional protein domains and the like, of either two different proteins or the same protein. As used herein, "functional fragment" or "portion" is intended to refer to less than the entire mature or native protein which is sufficient to retain one or more of the desired biological activities of the mature or native protein (e.g., sufficient to retain a therapeutic or ameliorative biological activity with respect to a disorder to be treated). Thus, amino acid sequences or polypeptides can be modified, for example, polypeptide sequences into which amino acids have been inserted, deleted and/or substituted in such a manner that the modifications do not substantially interfere with the polypeptide's ability to encode a functional agent.

In some embodiments, one protein of the polypeptide composition is a peptide having a desired activity, while the other polypeptide delivers or targets the polypeptide having a desired activity to a specific cell or tissue. As used herein, the phrase targeting ligand or binding peptide refers to an amino acid sequence which serves to direct and deliver an agent (e.g., protein, polypeptide) to a specific site for the desired activity. In particular embodiments, the desired activity of one of the polypeptides is a therapeutic or prophylactic activity (e.g., treatment, replacement, inhibition, prevention, enhancement, reduction or amelioration). For example, in some embodiments, the polypeptide compositions described herein comprise one or more enzymes and/or proteins that are deficient in a lysosomal storage disease/disorder. For instance, the disclosed compositions may comprise one or more therapeutic agents comprising or consisting of an amino acid sequence derived from one or more of aspartylglucosaminidase, acid lipase, cysteine transporter, Lamp-2, α-galactosidase A, lipoprotein lipase (LPL), ceramidase, α-L-fucosidase, β-hexosaminidase A, β-glucoronidase, GM2 ganglioside activator protein, α-D-mannosidase, β-D-mannosidase, arylsulphatase A, saposin B, neuraminidase, α-N-acetylglucosaminidase, phosphotransferase, phosphotransferase, L-iduronidase, iduronate-2-sulphatase, idursulfase, heparan-N-sulphatase, heparin sulfamidase, α-N-acetylglucosaminidase, N-acetyltransferase, N-acetylglucosamine 6-sulphatase, galactose 6-sulphatase, (β-galactosidase, N-acetylgalactosamine 4-sulphatase, N-acetylglucosamine 6-sulfatase, hyalurono-glucosaminidase, multiple sulphatases, palmitoyl protein thioesterase, tripeptidyl peptidase I, acid sphingomyelinase, α-galactosidase B, sialic acid, and functional fragments, subunits and combinations of the above. In certain embodiments, one of the proteins (e.g., the therapeutic protein) of a polypeptide composition comprises N-acetyl-alpha-glucosaminidase (NaGlu), particularly human NaGlu or a functional portion, fragment, variant, mutant or derivative of NaGlu. Loss of the lysosomal enzyme NaGlu is believed to be responsible for the lysosomal storage disorder, Sanfilippo syndrome.

In some embodiments, one of the polypeptides of the polypeptide composition comprises a cell-surface receptor ligand and, in particular embodiments, the polypeptide is IGFII, one of the ligands of the IGFII/cation-independent mannose 6-phosphate receptor (IGFII/CI-MPR). The IGFII/CI-MPR recognizes mannose 6-phosphate (Man6-P) moieties added to oligosaccharides on newly synthesized lysosomal enzymes in mammalian cells. As the Man6-P interaction with the IGFII/CI-MPR regulates normal intracellular trafficking that brings newly synthesized enzymes to the lysosome, IGFII/CI-MPR is thought to be a receptor mechanism that could be used to deliver the lysosomal enzymes to cells. The above-described compositions would then rely on receptor-mediated transcytosis mechanisms to deliver the linked protein (e.g., therapeutic protein) to the cell of interest (e.g., endothelial cells, macrophage or neuronal cells). Physiologically, receptor-mediated transport is relied upon to transport macromolecules (e.g., proteins, polypeptides) into the cell, and generally involves ligand-recognition and binding of a macromolecule (e.g., and IGFI or IGFII moiety) to a specific receptor binding domain (e.g., the cation-independent mannose-6 phosphate receptor (CI-MPR), the IGFI receptor, the IGFII receptor or the IGFII/CI-MPR) on the targeted cells. Following recognition and binding of the ligand to the binding domain on the receptor, the receptor-ligand complex undergoes endocytosis by the cell (e.g., endothelial cells or macrophage) and the complex is thereby internalized. The ligand may then be transported across the abluminal membrane of the cell (e.g., an endothelial cell, a neuronal cell, a glial cell, a perivascular cell and/or a meningeal cell) and into the appropriate tissue (e.g., tissues of the central nervous system such as brain or spinal tissue). In certain embodiments described herein, a binding or targeting peptide of a polypeptide composition comprises SEQ ID NO. 4, amino acid residues 8 through 67 of IGFII.

Also contemplated herein is the inclusion of functional protein labels or tags into the disclosed compositions to provide additional means of isolating and/or detecting the translated polypeptide or protein. Suitable labels and tags are well known in the art and, for example, include, but are not limited to luciferase, green fluorescent protein, alkaline phosphatase, horseradish peroxidase, myc-tags, FLAG tags, eTags and polyhistidine tags. In a preferred embodiment, such labels and tags are capable of providing a detectable signal to facilitate identification of such labels or tags, for example upon distribution of the amino acid sequence encoding the polypeptide composition into the desired cells and tissues (e.g., CNS tissue).

The polypeptide compositions described herein which comprise two polypeptides connected by a linker sequence, can be synthetically produced (e.g., by chemical synthesis) or encoded for and expressed by (e.g., transcribed and translated) a polynucleotide (e.g., nucleic acid) sequence. As used herein, a "polynucleotide" refers to contiguous, covalently linked nucleic acid or nucleic acid molecules, such as deoxyribonucleic acid (DNA) or ribonucleic acid (RNA), oligonucleotides, fragments generated by any appropriate means known in the art (e.g., ligation or polymerase chain reaction (PCR)), and/or fragments generated by any of ligation, scission, endonuclease action, and exonuclease action. Polynucleotide molecules can be composed of monomers that are naturally-occurring nucleotides (such as DNA and RNA). In some embodiments, the polypeptide compositions described herein are encoded by the homologous polynucleotide sequences. The polynucleotides are produced using recombinant DNA technique, known to those with skill in the art (see, e.g., Sambrook et al., 1992). Generally, in accordance with the present invention, one or more targeting agents (e.g., a ligand/binding protein like IGFII or a biologically active fragment thereof) are operably linked to a nucleic acid or an amino acid sequence encoding a therapeutic agent (e.g., the enzyme NaGlu or a biologically active fragment thereof). In some of the polynucleotide molecules described herein, comprised of nucleotide sequences of at least two genes joined by a linker sequence, can produce fusion or chimeric polypeptides that may represent a hybrid of the two proteins. The polypeptide compositions described herein may also comprise suitable regulatory elements which can be cloned into an expression vector and expressed in a suitable host. Recombinant methods for designing, expressing and purifying fusion proteins are known in the art (see, e.g. Sambrook, et al., 1992).

Also contemplated herein are expression vectors containing the above-described polynucleotides and recombinant cells comprising the polynucleotides or expression vectors. An "expression vector" is a polynucleotide molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a promoter can be operably linked if the regulatory element modulates the activity of the promoter. A "recombinant" or "host" cell used for expression of a vector is a cell that contains a polynucleotide molecule, such as the polynucleotides described herein. Large amounts of proteins may be produced in vitro using such expression vectors and/or recombinant cells and, accordingly, contemplated herein are methods of producing the disclosed polypeptide compositions. Such methods involve culturing a recombinant and/or host cell comprising a polynucleotide (e.g., expression vector) under conditions suitable for expression of the polypeptide from the polynucleotide. Any cell with protein synthetic capacity may be used for this purpose (e.g., animal, bacterial, yeast or insect cells). If a particular protein modification is required, animal cells and, in particular, mammalian cells may be necessary. Cells that may be used to express the polypeptide compositions include, but are not limited to, HT1080, HF1156, Chinese hamster ovary (CHO) cells, CHO-K1 cells, HeLa cells, Vero cells, FAO (liver cells), human 3T3 cells, A20 cells, EL4 cells, HepG2 cells, J744A cells, Jurkat cells, P388D1 cells, RC-4B/c cells, SK-N-SH cells, Sp2/mIL-6 cells, SW480 cells, 3T6 Swiss cells and the like. Suitable conditions for protein expression in various cells/systems are dependent on the cells/system and well-known in the art (Sambrook et al., 1992).

Also contemplated are pharmaceutical compositions that can be administered to a subject (e.g., a subject with a disease or disorder) to achieve a desired therapeutic effect (e.g., distribution into the cells and tissues of interest). Pharmaceutical compositions contemplated herein include, for example, nucleic acid or amino acid sequences encoding one or more therapeutic agents (e.g., the lysosomal enzyme NaGlu), operably linked to one or more targeting ligands (e.g., a fragment of IGFII), or vector or cells comprising the nucleic acid or amino acid sequences. Such amino or nucleic acids may be administered alone, but are preferably administered in combination with at least one other agent or excipient (e.g., a pharmaceutically-acceptable carrier such as buffered saline, dextrose, and purified water).

Suitable pharmaceutically-acceptable carriers preferably stabilize the proteins, enzymes, nucleic acids, amino acids and/or polypeptides suspended or solubilized therein and facilitate the processing of such proteins, enzymes, nucleic acids, amino acids and/or polypeptides into pharmaceutical compositions which may be administered to a subject. The described pharmaceutical compositions can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means.

Pharmaceutical formulations suitable for parenteral administration can be formulated in aqueous solutions, preferably in physiologically compatible buffers such as physiologically buffered saline. Aqueous injection suspensions can contain substances which increase the viscosity of the suspension, such as sodium carboxymethyl cellulose, sorbitol, or dextran. Optionally, the suspension also can contain suitable stabilizers or agents which increase the solubility of the compounds to allow for the preparation of highly concentrated solutions. Further details on techniques for formulation and administration can be found in the latest edition of Remington's Pharmaceutical Science (Maack Publishing Co., Easton, Pa.). After pharmaceutical compositions have been prepared, they can be placed in an appropriate container and labeled for treatment of an indicated condition (e.g., for the treatment of Sanfilippo syndrome). Such labeling may include, but not be limited to instructions to calculate an effective amount of the pharmaceutical composition to be administered to the subject, appropriate dosing schedules, acceptable routes of administration and anticipated adverse effects.

Also contemplated are methods of delivering a therapeutic polypeptide to a subject in need thereof by administering the polypeptide compositions and/or expression vectors and/or recombinant cells disclosed herein, to a subject in need thereof. Further contemplated are methods of treating a lysosomal storage disorder (e.g., Sanfilippo syndrome) by administering an effective amount of the disclosed polypeptide compositions to a subject in need thereof. As used herein, the term "subject" is meant to refer to any mammal (e.g., human, mouse, rat, dog, cat, pig, monkey, horse), particularly humans. In certain embodiments, the subject is an adult, an adolescent or an infant. Also contemplated by the present invention is the administration of the compositions and/or performance of the methods of treatment in-utero. The compositions and methods disclosed herein may be administered using any of the above-described routes of administration and, in certain embodiments, the polypeptide compositions are administered parenterally.

As used herein, the phrase "effective amount" refers to the amount of therapeutic agent and/or polypeptide needed to achieve a desired clinical effect and is largely determined based on the total amount of the therapeutic agent contained in a pharmaceutical composition. Generally, an effective amount of a therapeutic agent is sufficient to achieve a meaningful benefit to the subject (e.g., treating, modulating, curing, preventing and/or ameliorating the underlying disease or condition). For example, an effective amount of a pharmaceutical composition described herein may be an amount sufficient to achieve a desired therapeutic and/or prophylactic effect, such as an amount sufficient to modulate lysosomal enzyme receptors or their activity to thereby treat such lysosomal storage disorder or the symptoms thereof. Generally, the amount of a therapeutic agent (e.g., a recombinant lysosomal enzyme) administered to a subject in need thereof will depend upon the characteristics of the subject. Such characteristics include the condition, general health, age, sex and body weight of the subject. One of ordinary skill in the art will be readily able to determine the appropriate dosages depending on these and other related factors. In addition, both objective and subjective assays may optionally be employed to identify optimal dosage ranges.

EXEMPLIFICATION

To maximize uptake of the lysosomal enzyme N-acetyl-alpha-glucosaminidase (Naglu), a cassette encoding residues 8-67 of the mature IGFII was fused in frame to the C-terminus of the full length human Naglu open reading frame. The design of this construct was similar glucoronidase-IGFII fusion protein described by LeBowitz et al. (PNAS 101(9): 3083-3088, 2004), who observed that cellular uptake of glucoronidase, through the IGFII cation-independent mannose-6-phosphate receptor, was greatly improved when fused to IGFII, which binds with high affinity to a distinct site on the receptor. To establish the benefit of such a fusion protein, two expression plasmids were generated (FIG. 3A), one expressing full length wild-type human Naglu and the other expressing the Naglu-IGFII fusion protein with a linker region consisting of 3 residues, glycine alanine proline (GAP) (LeBowitz, 2004).

Figure 9:
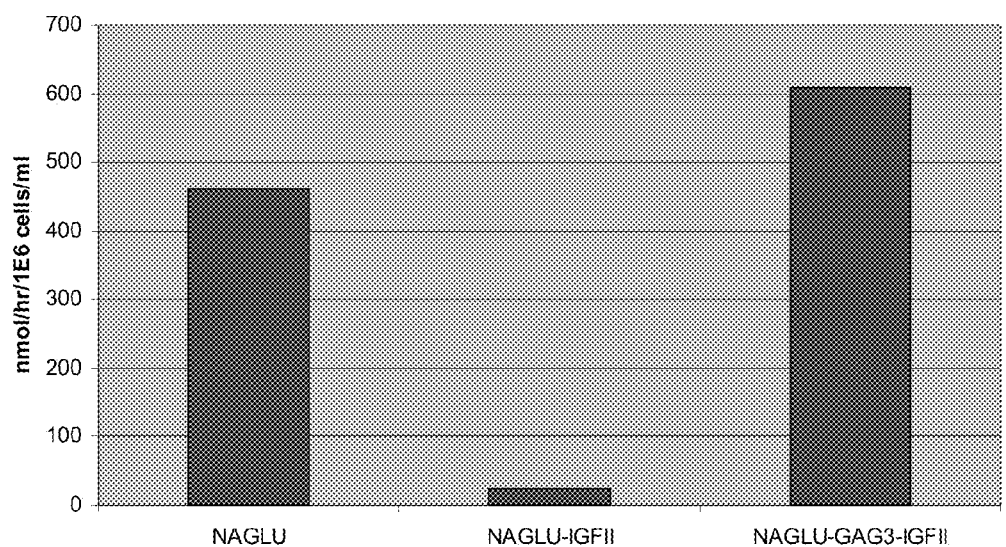
FIG. 9 illustrates a comparison of the activity levels of two different NaGlu-IGFII protein constructs (NaGlu-GAG$_3$-IGFII and NaGlu-IGFII) in HT1080 cells and demonstrates that, compared to wild-type NaGlu, NaGlu-GAG$_3$-IGFII has very high levels of activity, while NaGlu-IGFII has very little.
Figure 10:
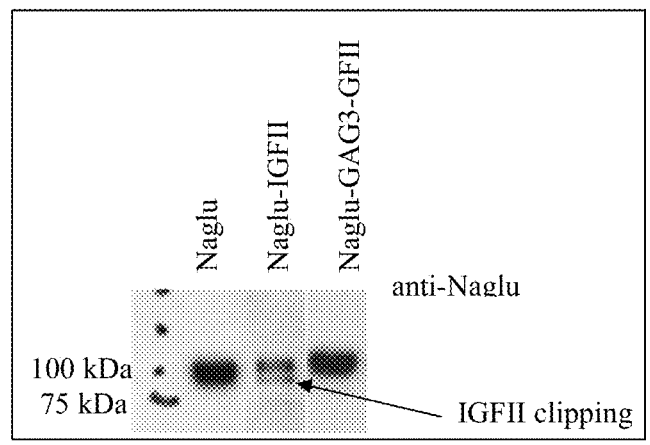
FIG. 10 illustrates the expression of NaGlu-GAG$_3$-IGFII and NaGlu-IGFII polypeptides by western blot and shows that the NaGlu-IGFII protein underwent degradation while wild-type NaGlu and NaGlu-GAG$_3$-IGFII did not.

HT1080 mammalian stable cell lines were generated for both wild-type Naglu and Naglu-IGFII. Following seeding of stable cell lines at $1\times10^6$ cells/ml and culture at 33° C. for 24 hours, protein expression was monitored in the conditioned media by western blot and activity determined by measuring the cleavage of the fluorogenic substrate 4MU-N-acetyl-alpha-D-glucosaminide. It was determined that activity, normalized by cell number, of Naglu-IGFII was 10 fold lower than that observed for untagged Naglu (see FIG. 9). By western blot, when sample load was normalized by cell number, it was apparent that Naglu-IGFII expression was significantly less than untagged Naglu (FIG. 10). Furthermore, there was also a significant amount of degradation occurring during Naglu-IGFII expression as evidenced by the lower molecular weight band running beneath the upper band in the Naglu-IGFII lane of the western blot (arrow, FIG. 10). This level of expression and breakdown was observed in all Naglu-IGFII stable clones developed which encompassed 3 separate stable transfections. In fact, when analyzing expression level and activity of various Naglu-IGFII clones, there was a very obvious correlation between the amount of degradation observed by western blot and the level of Naglu-IGFII activity in the sample. Thus, clones displaying higher levels of Naglu-IGFII in the conditioned media typically had a corresponding higher level of degradation on western blots. It was suspected that the Naglu-IGFII was relatively inactive due to the placement of the IGFII protein, and that the level of activity observed in samples taken from Naglu-IGFII clones was primarily due to clipping of the IGFII protein, resulting in an increased level of active, untagged Naglu in the cell-conditioned media samples.

Figure 3B:
FIG. 3B illustrates a NaGlu-IGFII construct joined by the linker of SEQ ID NO. 2 (NaGlu-GAG$_3$-IGFII).
Figure 11:
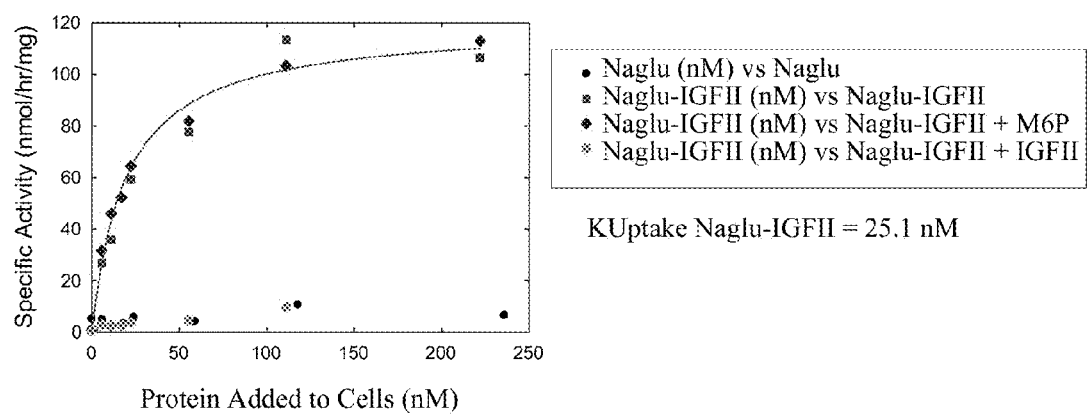
FIG. 11 illustrates the uptake of the NaGlu-GAG$_3$-IGFII polypeptide by human fibroblast cells (HF1156) and demonstrates that NaGlu-GAG$_3$-IGFII was readily taken-up by human cells.

It was hypothesized that increasing the linker length between Naglu and IGFII might improve the expression and activity of the Naglu-IGFII fusion protein by allowing for a more conformationally stable folded protein and/or prevent any potential interference between IGFII and the Naglu active site. To increase the linker length, complementary oligos were generated consisting of glycine alanine glycine repeats flanked by the original gap linker, which is encoded by an AscI restriction endonuclease site. The oligo was then ligated into the AscI site. In this ligation, 3 gag oligos were incorporated into the linker, resulting in a linker that was 57 amino acids long (FIG. 3B and FIG. 8). Stable clones generated from this construct yielded Naglu-GAG$_3$-IGFII protein that was as active (FIG. 9) and expressed to similar levels (FIG. 10) as Naglu. This confirmed that a longer linker allowed for proper folding and enzymatic activity of the Naglu-IGFII fusion protein. Furthermore, recombinant Naglu-GAG$_3$-IGFII and Naglu were tested for uptake in human fibroblast cells (HF1156). Naglu-GAG$_3$-IGFII was readily taken up by the cells, and that uptake was inhibited by IGFII but not mannose 6-phosphate (M6P), in a dose-dependent manner (FIG. 11). As expected, recombinant Naglu, lacking M6P, showed no uptake in the cells (FIG. 11).

Thus, the inventors surprisingly discovered a peptide linker which resulted in a highly expressed and active NaGlu-IGFII polypeptide. From this work, it is believed that a longer linker (e.g., longer than 3 amino acids), resulted in the proper folding/activity of the protein and prevented its degradation. Accordingly, this and similar peptide linkers can be used generally to link other proteins and create heterologous polypeptides.

While certain compositions and methods of the present invention have been described with specificity in accordance with certain embodiments, the following examples serve only to illustrate the compounds of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

What is claimed is:

1. An isolated polypeptide linker comprising the amino acid sequence of SEQ ID NO: 1, except one or more alanine residues of the amino acid sequence of SEQ ID NO: 1 are substituted with a serine residue.

2. The isolated polypeptide linker of claim 1, wherein said linker further comprises the amino acid sequence glycine-alanine-proline (GAP) at the C-terminus of said linker.

3. An isolated fusion polypeptide composition comprising the linker of claim 1, further comprising a first peptide and a second peptide, wherein said linker is disposed between the first peptide and the second peptide.

4. The isolated fusion polypeptide composition of claim 3, wherein said first peptide comprises the amino acid sequence of SEQ ID NO: 4.

5. The isolated fusion polypeptide composition of claim 3, wherein said second peptide comprises a receptor binding domain.

6. The isolated fusion polypeptide composition of claim 3, wherein said second peptide comprises the amino acid sequence of SEQ ID NO: 6.

7. The isolated fusion polypeptide composition of claim 3, wherein said first peptide comprises the amino acid sequence of SEQ ID NO: 4 and wherein said second peptide comprises the amino acid sequence of SEQ ID NO: 6.

8. A pharmaceutical fusion composition comprising the isolated fusion polypeptide composition of claim 7 and an acceptable carrier.

9. An isolated polypeptide linker comprising the amino acid sequence of SEQ ID NO: 2, except one or more alanine residues of the amino acid sequence of SEQ ID NO: 2 are substituted with a serine residue.

10. An isolated fusion polypeptide composition comprising said linker of claim 9, further comprising a first peptide and a second peptide; wherein said linker is disposed between the first peptide and the second peptide.

11. The isolated fusion polypeptide composition of claim 10, wherein said first peptide comprises the amino acid sequence of SEQ ID NO: 4.

12. The isolated fusion polypeptide composition of claim 10, wherein said second peptide comprises a receptor binding domain.

13. The isolated fusion polypeptide composition of claim 10, wherein said second peptide comprises the amino acid sequence of SEQ ID NO: 6.

14. The isolated fusion polypeptide composition of claim 10, wherein said first peptide comprises the amino acid sequence of SEQ ID NO: 4 and wherein said second peptide comprises the amino acid sequence of SEQ ID NO: 6.

15. A pharmaceutical fusion composition comprising the isolated fusion polypeptide composition of claim 14 and an acceptable carrier.

16. An isolated polypeptide fusion composition comprising a first peptide, a second peptide, and a polypeptide linker; wherein said linker comprises the amino acid sequence of SEQ ID NO: 1, except one or more alanine residues of the amino acid sequence of SEQ ID NO: 1 are substituted with a serine residue, and wherein the isolated fusion polypeptide composition comprises one or more sequential repeats of said linker disposed between said first peptide and said second peptide.

17. The isolated fusion polypeptide composition of claim 16, wherein said linker further comprises the amino acid sequence glycine-alanine-proline (GAP) at the C-terminus of said linker.

18. The fusion polypeptide composition of claim 16, wherein said first peptide comprises the amino acid sequence of SEQ ID NO: 4.

19. The fusion polypeptide composition of 16, wherein said second peptide comprises the amino acid sequence of SEQ ID NO: 6.

20. The isolated fusion polypeptide of claim 3, wherein said fusion polypeptide comprises three sequential repeats of said linker disposed between said first peptide and said second peptide.

21. The isolated polypeptide linker of claim 1, wherein said linker comprises three sequential repeats of said linker.

22. The isolated polypeptide linker of claim 21, wherein said linker further comprises the amino acid sequence glycine-alanine-proline (GAP) at the C-terminus of said linker.

\* \* \* \* \*